United States Patent [19]

Ok et al.

[11] Patent Number: 5,374,746
[45] Date of Patent: Dec. 20, 1994

[54] L-TALOPYRANOSIDE DERIVATIVES AND PROCESS FOR THE PREPARATION OF SAME

[75] Inventors: Kwang D. Ok; Moon S. Kim; Dong Y. Jung, all of Suwon, Rep. of Korea

[73] Assignee: Dong-A Pharmaceutical Co., Ltd., Seoul, Rep. of Korea

[21] Appl. No.: 77,952

[22] Filed: Jun. 18, 1993

Related U.S. Application Data

[62] Division of Ser. No. 800,038, Nov. 29, 1991, abandoned.

[30] Foreign Application Priority Data

Nov. 30, 1990 [KR] Rep. of Korea .................. 90/19582
Nov. 30, 1990 [KR] Rep. of Korea .................. 90/19583

[51] Int. Cl.$^5$ ............................................. C07D 309/02
[52] U.S. Cl. ............................................................ 549/417
[58] Field of Search ........................................ 549/417

[56] References Cited

U.S. PATENT DOCUMENTS 3,590,028 6/1971 Arcamone et al. ............... 260/210
3,616,242 10/1971 Belloc et al. ........................ 424/123

FOREIGN PATENT DOCUMENTS 62-145096 6/1987 Japan .
62-145097 6/1987 Japan .
63-141992 6/1988 Japan .
89/15375 10/1989 Rep. of Korea .
90/17084 10/1990 Rep. of Korea .

OTHER PUBLICATIONS

CA 69:27654c, 1968.
CA 72:55834s, 1970.
CA 81:13750s, 1974.
Towson, T., J. Org. Chem., 48, pp. 3507-3510, 1983.
CA 79:92492u, 1973.
CA 92:111238c, 1980.
CA 98:215917p, 1983.
CA 111:97634f, 1989.
Ok et al., *Carbohydrate Research*, 169, pp. 69-81, 1987.
Raddo et al., *Carbohydrate Research*, 153, pp. 141-145, 1986.
Miura et al., *The Journal of Antibiotics*, 39(5), pp. 731-735, 1986..

*Primary Examiner*—C. Warren Ivy
*Assistant Examiner*—Ba K. Trinh
*Attorney, Agent, or Firm*—Bacon & Thomas

[57] ABSTRACT

The present invention relates to a L-talopyranoside derivative of the formula (I):

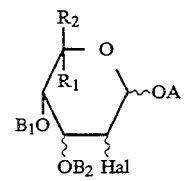

(I)

wherein,

A is hydrogen atom, a lower alkyl group having 1 to 5 carbon atoms, or a hydroxyl-protecting group;

$B_1$ and $B_2$, the same or different from each other, are independently hydrogen atom or a hydroxyl-protecting group;

$R_1$ and $R_2$ may form a alkylene group with a carbon atom of 5-position of the sugar skeleton, or one of them is hydrogen atom and the other is $CH_2X$ wherein, X is hydrogen, or a protected or un-protected hydroxyl group.

Provided that, the following compounds are excepted:

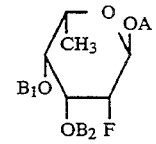

wherein, $B_1$ and $B_2$ are independently hydrogen atom or acetyl. L-talopyronoside derivatives of the present invention is a very useful intermediate for the synthesis of anthracycline antibiotics having an antitumor activity. The process according to the invention has an advantage of significant reduction in the production cost and therefore expected to be very useful for the preparation of anthracycline antibiotics in an industrial scale.

1 Claim, No Drawings

L-TALOPYRANOSIDE DERIVATIVES AND PROCESS FOR THE PREPARATION OF SAME

This application is a division of application Ser. No. 07/800,038, filed Nov. 29, 1991, now abandoned.

FIELD OF THE INVENTION

The present invention relates to a L-talopyranoside derivative which is a very useful intermediate for synthesis of anthracyclines and to a process for the preparation of the same.

DESCRIPTION OF PRIOR ART

Anthracycline antibiotics are known to be very useful anticancer agents.

As anthracycline anticancer agents, there have been known Daunomycin (U.S. Pat. No. 3,616,242) and Adriamycin (U.S. Pat. No. 3,590,028), which show a broad anti-cancer spectrum and an anti-tumor activity against the tumors and are widely used as chemotherapeutic agents for cancer.

These compounds may be represented by the following formula (A):

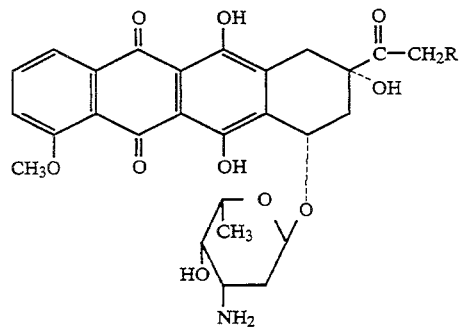

wherein, R represents hydrogen atom or a hydroxyl group. However, Daunomycin, a compound of the above formula(A) in which R is hydrogen atom, and Adriamycin, a compound of the above formula(A) in which R is a hydroxyl group have severe adverse effects such as leukopenia, depilation or myocardiac disorder when used for cancer-chemotherapy.

Extensive studies have been conducted to avoid the above drawbacks and the various derivatives in which the structure of the sugar skeleton is modified have been reported.

For example, inter alia the compound variants which are substituted by iodine in 2-position of the sugar skeleton were disclosed in U.S. Pat. No. 4,562,177 and those substituted by fluorine were disclosed in Japanese Patent Laid-Open Publication Nos. 62-145,097 and 63-141,992 and Korean Patent Application Nos. 89-15,375 and 90-17,084.

These compound variants may be represented by the following formula(B):

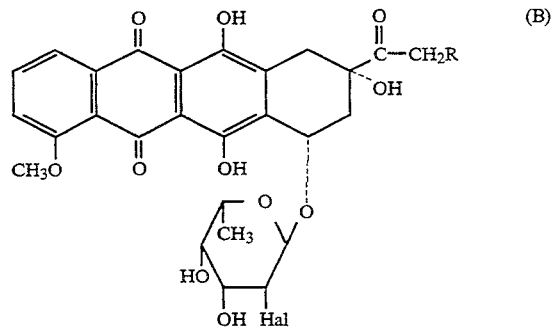

wherein, R is hydrogen atom, a hydroxyl group, a group of the formula;

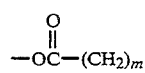

H in which m is an integer of 0 to 6, a group of the formula;

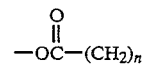

COOH in which n is an integer of 0 to 6, or a group of the formula;

in which Y is

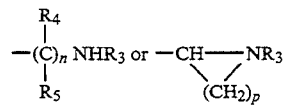

in which $R_3$ is hydrogen atom, a straight or branched alkyl group having 1 to 10 carbon aroma, or a straight or branched alkoxycarbonyl group having 1 to 10 carbon aroma, $R_4$ and $R_5$ are independently hydrogen atom or an alkyl group having 1 to 5 carbon aroma, n is an integer of 0 to 10, p it an interger of 1 to 5; and Hal is a halogen atom, for example fluorine, chlorine, iodine or bromine.

These compounds were known to have an improved anti-tumor activity as well as a reduced toxicity. In particular, the compound into which amine group is introduced in 14-position has a high solubility in water and shows an excellent anti-tumor activity.

The structural characteristic of these compounds is that they are substituted by a halogen atom in 2'-position of the sugar skeleton. 2'-halogen substituted sugars are characterized by that their glycoside linkage is stable against hydrolysis using acid and that they show an increased anti-tumor activity as wall as a reduced toxcity due to properties of the halogen atom, in particular fluorine atom.

The preparation of 2,6-dideoxy-2-halo-α-L-talose derivatives, which are important intermediates for synthesis of anthracycline agents, are disclosed, for example in Japanese Patent Laid-Open Publication No. 62-145,096, Carbohydrate Research 169, 69–81 (1987)

and J. Antibiotics, 39(5), 731–733 (1986) and may be shown by the following reaction scheme:

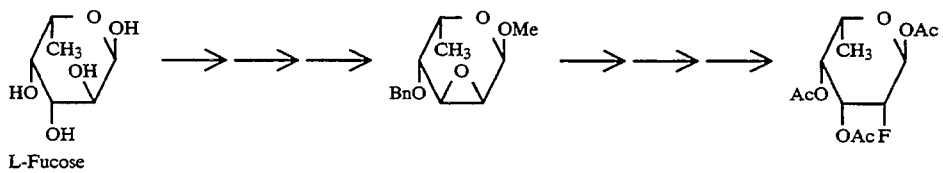

L-Fucose

However, the above known process starting from L-fucose to prepare 1,3,4-tri-O-acetyl-2,6-dideoxy-2-fluoro-α-L-talopyranose has some disadvantages such that it cannot be employed on an industrial scale because it requires multiple reaction steps, and L-fucose, a starting material, is very expensive(US$5,468/kg according to Aldrich Catalogues, '90–'91) and can not be available easily due to its limited supply.

Therefore, there still remains a need to develop intermediates for synthesis of anthracycline, which can be prepared by a simple process with a high yield. And there also remains a need to develop a process for the preparation of the intermediates which employs an inexpensive starting material and can be applied on an industrial scale.

SUMMARY OF THE INVENTION

An object of the invention is to provide a compound of the following formula (I):

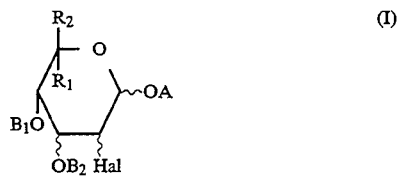

wherein,

A is hydrogen atom, slower alkyl group having 1 to 5 carbon atoms, or a hydroxyl-protecting group;

$B_1$ is a hydrogen atom or a hydroxyl-protecting group;

$B_2$ is a hydrogen atom or a hydroxyl-protecting group, or —$OB_2$ may form a ketone group together with the carbon atom of the 3-position of the sugar skeleton;

Hal is a halogen atom selected from the group consisting of fluorine, chlorine, iodine and bromine;

$R_1$ and $R_2$ may form an alkylene group with the carbon atom of the 5-position of the sugar skeleton, one of them is a hydrogen atom and the other is —$CH_2X$ wherein X is a hydrogen atom or a halogen atom selected from the group consisting of fluorine, chlorine, iodine and bromine, or $R_2$ and $B_1$ may together form a benzylidene group when $R_2$ is —$CH_2X$ and $B_1$ is a hydroxyl protecting group;

with the proviso that the following compounds are excepted:

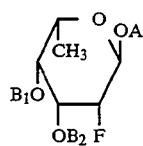

wherein, A is a hydrogen atom, a methyl or acetyl group; $B_1$ and $B_2$, which may be the same or different from each other, are independently a hydrogen atom or a hydroxyl-protecting group.

L-talopyranoside derivatives of the formula(I) are very useful for the synthesis of anthracycline anti-cancer agents such as 7-O-(2',6'-dideoxy-2'-halo-α-L-talopyranosyl) daunomycinone or 7-O-(2',6'-dideoxy-2'-halo-α-L-talopyrenosyl) adriamycinone, or its derivatives.

An object of the invention is to provide a process for preparing the compound of the formula (17-1):

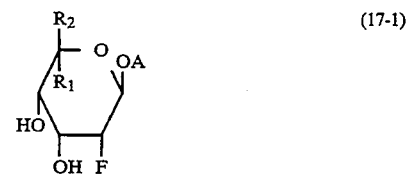

wherein A is hydrogen, a lower alkyl group having 1 to 5 carbon atoms, or a hydroxyl protecting group; and $R_1$ and $R_2$ are, independently, hydrogen or a lower alkyl group having 1 to 5 carbon atoms;

which comprises subjecting a compound of formula (12):

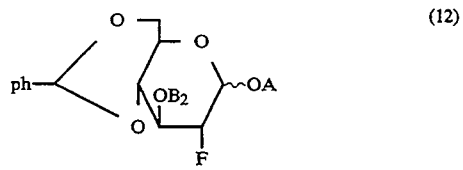

wherein $B_2$ is a hydroxyl-leaving group; Ph is phenyl; and A has the same meaning as defined above, to substitution in the presence of sodium benzoate in dimethyl formamide to give a compound of the formula (13):

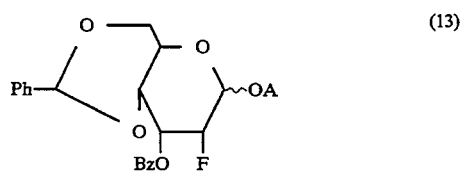

wherein Bz in benzoyl, and A has the same meaning as defined above, reacting the compound of formula (13) with N-halosuccineimide and barium carbonate in carbon tetrachloride to give a compound of the formula (14):

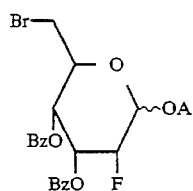

(14)

wherein A and Bz have the same meanings as defined above, reacting the compound of the formula (14) with a metal halide in the presence of an amine to give a compound of the formula (15):

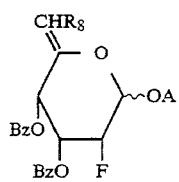

(15)

in which $R_8$ is hydrogen, and A and Bz have the same meanings as defined above, and subjecting the compound of the formula (15) to hydrogenation in the presence of a metal catalyst, for example palladium, Raney-nickel or platinum, to give a compound of formula (16-1):

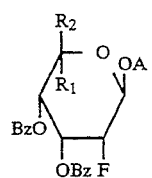

(16-1)

wherein A, $R_1$, $R_2$ and Ba have the same meanings as defined above, and subjecting the compound of formula (16-1) to benzoylation in the presence of sodium methoxide in methanol to give the compound of (17-1).

The compound of the formula (13) is novel and can be prepared by reacting a compound of the formula (12):

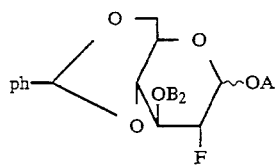

(12)

wherein $B_2$ is a hydroxyl-leaving group, and A has the same meaning as defined above,
with sodium benzoate, or
by reacting a compound of the formula (9):

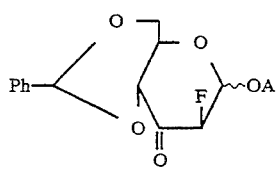

(9)

wherein A has the same meaning as defined above, with triethylamine to give a compound of the formula (10):

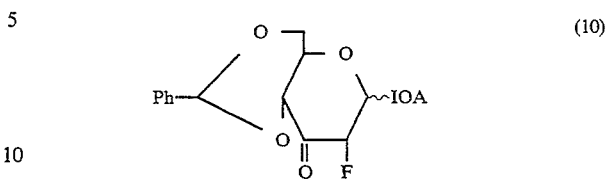

(10)

wherein A has the same meaning as defined above, reacting the compound of the formula (10) with sodium borohydride to give a compound of the formula (11):

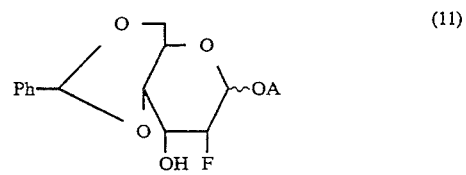

(11)

wherein, A has the same meaning as defined above, and reacting the compound of the formula(11) with benzoyl chloride.

A more complete appreciation of the invention, and many of the attendant advantages thereof, will be readily perceived as the said invention becomes better understood by reference to the following detailed description of the invention. Other objects, advantages and features of the present invention will also become apparent to those skilled in the art from the following discussion.

DETAILED DESCRIPTION OF THE INVENTION

A need to provide a process for preparing anthracyclines which can be applied on an industrial scale with a low cost, prompted to the present inventors to search for a cheap starting material which can replace the conventional expensive starting material, L-fucose and to search for a simple process for preparing an intermediate for synthesis of anthracyclines. α-D-glucose, which is employed in place of L-fucose as a starting material according to the process of the invention is very cheap(US$4.33/kg, Aldrich Catalogues '90-'91) compared with L-fucose(US$5,468/kg, Aldrich catalogues '90-'91). Thus, the price of α-D-glucose is 1/1262 times lower than that of L-fucose. Further, α-D-glucose is easily, available in large quantities without difficulty.

L-talopyranoside derivatives according to the invention, which are useful intermediates for the preparation of anthracyclines, may be prepared by starting from α-D-glucose. According to the invention, L-talopyranoside derivatives may be prepared by the following reaction schemes 1 and 2:

(Reaction scheme 1)
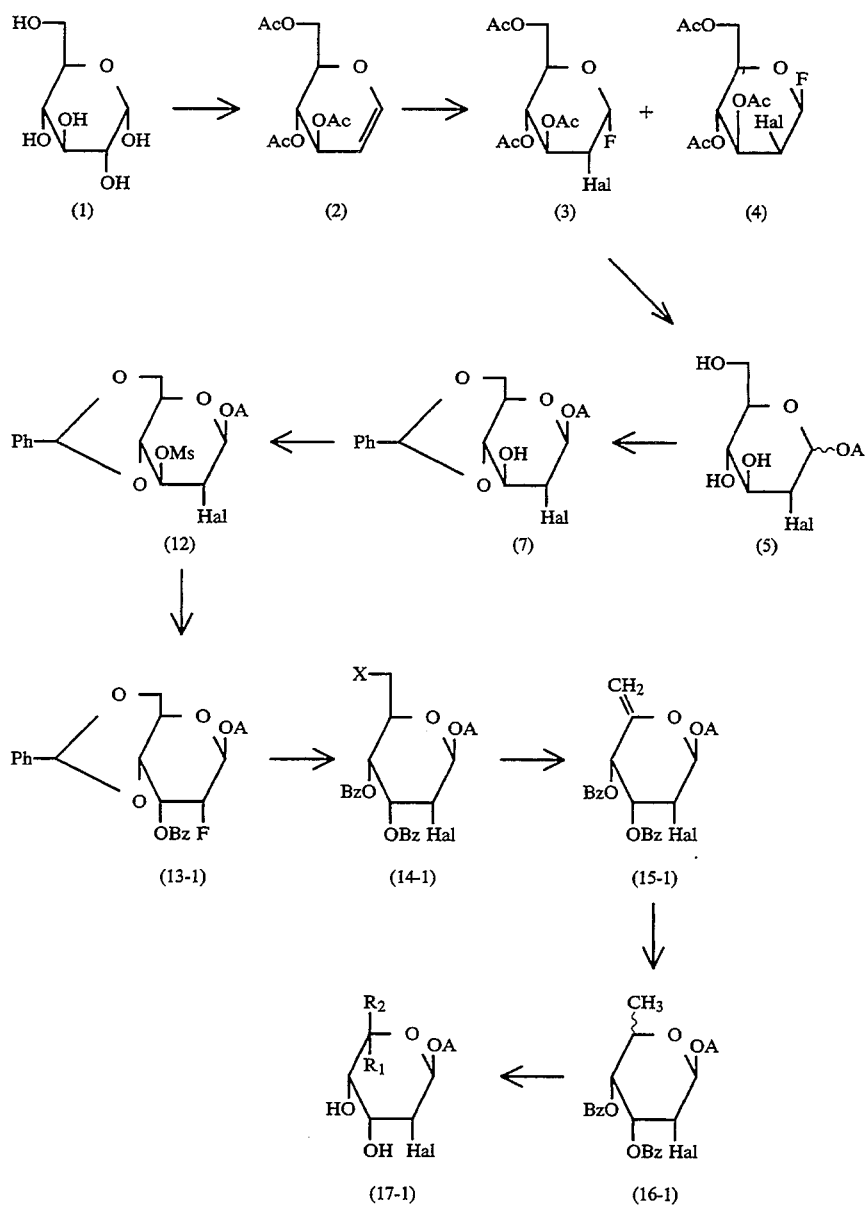
(Ac = Acetyl, Ph = Phenyl, Ms = Mesyl, Bz = Benzoyl)
(Reaction scheme 2)
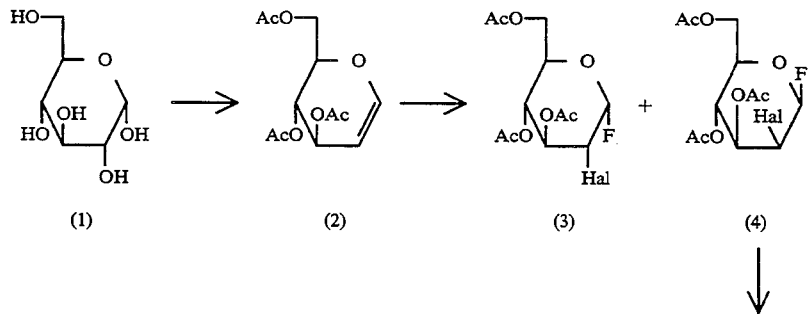

-continued
(Reaction scheme 2)

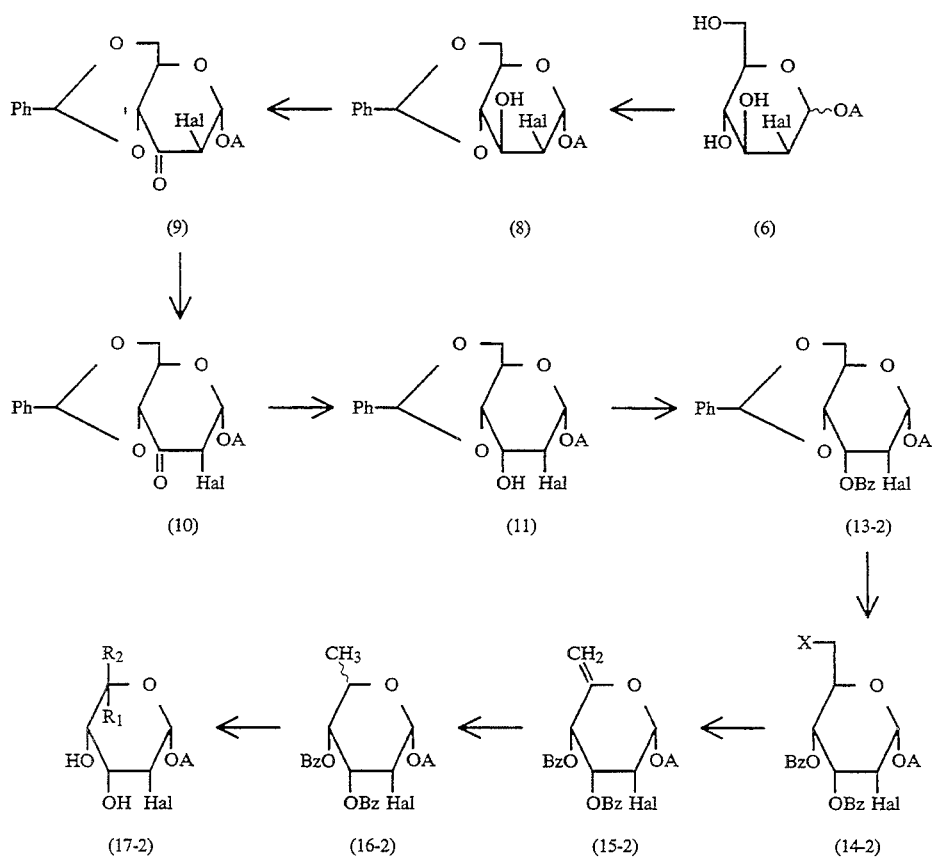

(Ac = Acetyl, Ph = Phenyl, Ms = Mesyl, Bz = Benzoyl)

In the above schemes, A and X have the same meanings as defined above.

Each reaction steps will be described in detail herein after. First, tri-O-acetyl-D-glucal(2) is prepared from α-D-glucose(1) by the known methods, for example the process described in Methods in Carbohydrate Chemistry, Academic Press, Roy L. Whistler, 2, p. 405–408. Then, tri-O-acetyl-D-glucal(2) is reacted with fluorine in the presence of solvent with reference to the method described in Carbohydrate Research 153, p. 141–145 (1986) to give a mixture of compounds (3) and (4) in a ratio of 6:4.

As a solvent, water or organic solvent such as acetonitrile or mixtures thereof may be employed.

According to the scheme 1, the compound (3) is reacted with acetyl chloride and methanol in benzene to give compound (5) as a mixture of α- and β-anomer in a ratio of 2:3.

The compound (5) is reacted with benzaldehyde dimethyl acetel to give compound (7).

The compound (7) is mesylated in 3-hydroxyl group by reacting with mesyl chloride and the compound (12) obtained is reacted with a metal salt of organic or inorganic acid to give the compound (13-1). Metal salts of organic or inorganic acid which can be employed may include sodium or potassium salts of organic or inorganic acid. For example, sodium benzoate or sodium acetate are advantageously employed.

In addition to mesyl chloride, para-toluenesulfonyl chloride or trifluoromethane sulfonyl anhydride may be used as a leaving group reagent.

Thus prepared compound (13-1) is reacted with N-halosuccinimide and barium carbonate in carbon tetrachloride to give the compound of the formula (14-1) in which X is a halogen atom. The reaction temperature varies between room temperature and the boiling point of the solvent employed. The boiling point of the solvent is preferred.

Besides, the compound (13-1) is first debenzylidenated and halogenated to give the compound of the formula (14) in which X is a halogen atom.

The compound (14-1) is reacted with a metal halide in the presence of amine to give the compounds (15-1). As a metal halide, there may be employed for example silver halide. As an amine solvent, for example pyridine is used. For this reaction, in addition to metal halide, other metal salts, sodium methoxide, DBU(1,8-diazabicyclo [5,4,0] undecen-7-ene) or soda lime also may be employed to promote the formation of double bond.

As a metal halide, silver halide, in particular silver fluoride is preferred.

The compounds (15-1) are subjected to hydrogenation by using a metal reducing catalyst such as palladium, Raney-Nickel or platinium to give the compound (16-1). As a metal reducing catalyst, Palladium/Carbon is advantageously employed. The hydrogenation may carried out under room or atmospheric or high pressure and at the temperature between room temperature and boiling point of the solvent employed. Preferably, the reaction is carried out at room temperature under atmospheric pressure. Further, if necessary, steric isomers of the compound (16-1) may be purified by silica gel column chromatography using, for example, methylene chloride as an eluant. L-isomer of the compounds (16-1) is preferred.

According to the scheme 2, the compound (4) prepared as described in the scheme 1 is reacted with acetyl chloride and methanol in benzene to give the compound (6) as a mixture of α-and β-anomer in a ratio of 8:1.

The compound (6) is reacted with benzaldehyde dimethyl acetel to give the compound (8). The compound(8) which is in a allo-form is also obtained from the gluco-form compound (7) by an inversion In 3-position hydroxyl group.

The compound (8) is oxidized in 3-position and the resulting compound (9) is treated with an alkali to give the compound (10), which is subjected to hydrogenation. The compound (11), which is obtained with a high yield from the compound (10), is then benzoylated to give the compounds (13-2).

In oxidation of the compound (8), pyridinium chlorochormate, dimethyl sulfoxide or anhydrous acetic acid is employed as an oxidizing agent. For the hydrogenation of the compound (10), metal reducing catalysts or metal hydrides are properly used as a reducing agent. In particular, sodium borohydride may be advantageously employed. The benzoylation of the compound (11) is carried out in pyridine by using benzoyl chloride. Thus obtained compound (13-2) is treated as shown in the scheme 1 to give the compound (16-2).

Then, the compounds (16-1) and (16-2) may be debenzoylated by using sodium methoxide to give the compounds (17-1) and (17-2), respectively, which can be preferably further subjected to acetolysis and halogenetion in order to be reacted with adriamycinon or daunomycinon.

The acetolysis may be carried out by using anhydrous acetic acid, acetic acid and a catalytic amount of sulfuric acid in the presence of nitromethane solvent. Subsequently, the halogenetion may be carried out by reacting with titanium tetrabromide.

Thus obtained halogenated compounds (I) in which $B_1$ and $B_2$ are acetyl group may be reacted adriamycinon or daunomycinon to give anthracyclines as follows:

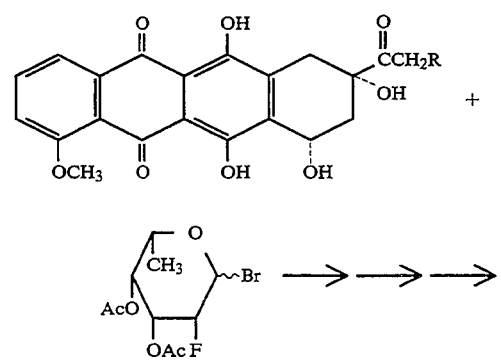

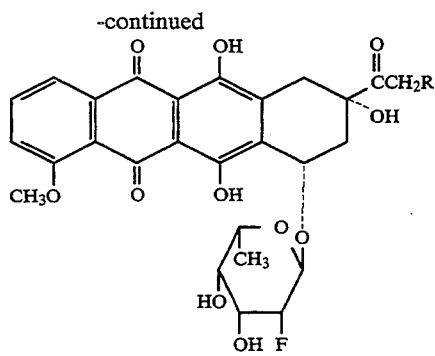

wherein, R is hydrogen atom, a hydroxyl group, a group of the formula;

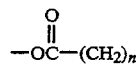

H in which m is an integer of 0 to 6, a group of the formula;

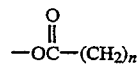

COOH in which n is an integer of 0 to 6, or a group of the formula;

in which Y is

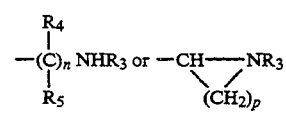

in which $R_3$ is hydrogen atom, a straight or branched alkyl group having 1 to 10 carbon atoms, or a straight or branched alkoxycarbonyl group having 1 to 10 carbon atoms, $R_4$ and $R_5$ are independently hydrogen atom or an alkyl group having 1 to 5 carbon atoms, n is an integer of 0 to 10 and p is an integer of 1 to 5.

3,4-di-O-acetyl-2,6-deoxy-2-fluoro-α-L-talopyranosyl bromide obtained in the above and daunomycinone were reacted together in the presence of mercuric oxide, mercuric bromide and molecular sieve 3A in anhydrous methylene chloride and the resulting compounds are deprotected by deacetylating the sugar skeleton to give daunomycin derivatives (B) in which R is hydrogen atom.

Moreover, adriamycin derivatives (B) in which R is hydroxyl group may be prepared by brominating adriamycin derivatives in which R is hydrogen atom with bromine and reacting with sodium formate and then 40% aqueous acetic acid solution. When compounds (B) in which R is bromine are obtained, they are reacted with monosodium Dimelate or sodium t-butyloxycarbonyl glycinate and then deprotected to give the desired adriamycin or daunomycin derivatives.

The invention being generally described, a more complete understanding can be attained by reference to the examples which are provided herein for purposes of illustration only, and are not intended to limit the invention unless otherwise specified.

EXAMPLE 1

Preparation of 3,4,6-tri-O-acetyl-2-deoxy-2-fluoro-α-D-glucopyranosyl fluoride(formula 3) and of 3,4,8-tri-O-acetyl-2-deoxy-2-fluoro-β-D-mannopyranosyl fluoride(formula 4)

In 50 ml of mixed solvent of acetonitrile and water(10:1) were dissolved 5 g of 2,4,6-tri-O-acetyl-glucal and 5% He—F$_2$ gas was bubbled therein at room temperature. The reaction was carried out until the starting material was disappeared. The resulting reaction mixture was concentrated under the reduced pressure and subjected to silica gel column chromatography using chloroform-ethyl acetate(10:1) as an eluant, to give 2.57 g of the compound of the formula(3) and 1.80 g of the compound of the formula(4).

NMR (CDCl$_3$, ppm)

Compound(3) : 5.78(d,d, 1H, H-1, $J_{H-1-F-1}$=52.6 Hz, $J_{H-1-H-2}$=2.7 Hz), 4.60(d,d,d,d, 1H, H-2, $J_{H-2-F-2}$=48.1 Hz, $J_{H-2-F-1}$=23.7 Hz, $J_{H-2-H-3}$=9.6 Hz, $J_{H-2-H-1}$=2.7 Hz)

Compound(4) : 5.51(d,d, 1H, H-1, $J_{H-1-F-1}$=49.2 Hz, $J_{H-1-F-2}$=12.9 Hz), 5.13(d,d,d, 1H, H-3, $J_{H-3-F-2}$=21.6 Hz)

EXAMPLE 2

Preparation of methyl-4,6-O-benzylidene-2-deoxy-2-fluoro-β-D-glucopyranoside(formula 7)

2 g of 3,4,6-tri-O-acetyl-2-deoxy-2-fluoro-α-D-glucopyranosyl fluoride (formula 3) prepared in Example 1 were dissolved in a mixture of methanol(80 ml) and benzene(30 ml), 12 ml of acetyl chloride were slowly added thereto and the mixture was refluxed for 12 hours. The resulting reaction solution was concentrated under the reduced pressure to give 1.18 g of methyl-2-deoxy-2-fluoro-D-glucopyranoside.

The compound(1.18 g) obtained in the above was dissolved in 16 ml of dimethyl formamide, and 1.2 g of benzaldehyde dimethyl acetal and a catalytic amount(120 mg) of p-toluene sulfonic acid monohydrate were successively added thereto. The mixture was reacted at 50° C. for 1 hour and dimethyl formamide was distilled off under the reduced pressure. The residues were chromatographed on the column packed with silica gel using toluene:ethyl acetate=6:1 as an eluant to give α-type(858 mg) and β-type(762 mg) of methyl-4,6-O-benzylidene-2-deoxy-2-fluoro-D-glucopyranoside.

m.p. : 160°–162° C. for α-type compound 188°–189° C. for β-type compound

EXAMPLE 3

Preparation of methyl-4,6-O-benzylidene-2-deoxy-2-fluoro-α-D-mannopyranoside(formula 8)

By following the procedure in Example 2 except that 1.59 g of 3,4,6-tri-O-acetyl-2-deoxy-2-fluoro-β-D-mannopyranosyl fluoride prepared in Example 1 were employed, there were obtained 1.144 g of methyl-4,6-O-benzylidene-2-deoxy-2-fluoro-α-D-mannopyranoside.

Rf=0.5 (n-hexane:ether=1:2)

NMR (CDCl$_3$, ppm) 7.33–7.50 (m, 5H, Ph), 5.57 (s, 1H, Ph—CH) 4.85 (m, 1H, H-1), 4.73 (m, 1H, H-2, $J_{H-2-F}$=48 Hz) 3.70–4.30 (m, 5H, H-3, H-4, H-5, H-6a, H-6b) 3.41 (s, 3H, —OCH$_3$), 2.31 (br.s, 1H, —OH)

EXAMPLE 4

Preparation of methyl-4,6-O-benzylidene-2-deoxy-2-fluoro-α-D-manno-hexopyranoside-3-ulose(formula 9)

In 34 ml of methylene chloride were dissolved 1.90 g of methyl-4,6-O-benzylidene-2-deoxy-2-fluoro-α-D-mannopyranoside prepared in Example 3, 5.78 g of pyridinium chlorochromate and 5.78 g of molecular sieve 3A were added thereto and the mixture was reacted at room temperature overnight. After completion of the reaction, the reaction mixture was filtered with Florosil$^R$ and concentrated under the reduced pressure to give the desired compound (1.40 g).

Rf=0.2 (toluene:ethyl acetate=3:1)

NMR (CDCl$_3$, ppm) 7.33–7.49 (m, 5H, Ph), 5.61 (s, 1H, Ph—CH) 5.10 (d, 1H, H-1), 4.67 (d,d, 1H, H-2, $J_{H-2-F}$=49 Hz) 3.44 (s, 3H, —OCH$_3$)

EXAMPLE 5

Preparation of methyl-4,6-O-benzylidene-2-deoxy-2-fluoro-α-D-glucohexopyranoside-3-ulose (formula 10)

In 3 ml of tetrahydrofuran were dissolved 910 mg of methyl-4,6-O-benzylidene-2-deoxy-2-fluoro-α-D-manno-hexopyranoside-3-ulose prepared in Example 4. 1.36 ml of triethylamine were added thereto and the mixture was refluxed with stirring for 5 hours. The resulting reaction mixture was cooled to room temperature and worked up. The residues were column chromatographed using toluene:ethyl acetate=4:1 as an eluant to give the desired compound with a quantatitive yield.

Rf=0.4 (toluene:ethyl acetate=3:1)

NMR (CDCl$_3$, ppm) 7.33–7.52 (m, 5H, Ph), 5.54 (s, 1H, Ph—CH) 5.29 (d,d, 1H, H-1) 5.03 (d,d,d, 1H, H-2, $J_{H-2-F}$=46.9 Hz) 4.42 (d,d, 1H, H-6a), 4.24 (d, d, 1H, H-4) 4.11 (d,d,d, 1H, H-5), 3.90 (d,d, 1H, H-6b) 3.49 (s, 3H, —OCH$_3$)

EXAMPLE 6

Preparation of methyl-4,6-O-benzylidene-2-deoxy-2-fluoro-α-D-allopyranoside(formula 11)

In a mixed solvent(20 ml) of methanol and water(3:1) were dissolved 252 mg of methyl-4,6-O-benzylidene-2-deoxy-2-fluoro-α -D-gluco-hexopyranoside-3-ulose prepared in Example 5, 41 mg of sodium borohydride were added thereto and the mixture was reacted with stirring for 20 min. After completion of the reaction, the reaction solution was concentrated, extracted with chloroform, washed with water and concentrated to give 253 mg of methyl-4,6-O-benzylidene-2-deoxy-2-fluoro-α-D-allopyranoside.

Rf=0.2 (toluene:ethyl acetate=6:1)

NMR (CDCl$_3$, ppm) 7.34–7.51 (m, 5H, Ph), 5.55 (5, 1H, Ph—CH) 4.97 (d,d, 1H, H-1, $J_{H-1-F}$=0, $J_{H-1-H-2}$=3.8 Hz) 4.51 (d,d,d, 1H, H-2), 4.52 (m, 1H, H-3) 4.40 (d,d, 1H, H-6a), 4.15 (d,d,d, 1H, H-5) 3.74 (d,d, 1H, H-6b), 3.51 (s, 3H, —OCH$_3$) 3.49 (m, 1H, H-4), 3.09 (d, 1H, —OH)

EXAMPLE 7

Preparation of
methyl-4,6-O-benzylidene-2-deoxy-2-fluoro-3-benzoyl-α-D-allopyranoside (formula 13-2)

In 5 ml of pyridine were dissolved 253 mg of methyl-4,6-O-benzylidene-2-deoxy-2-fluoro-α-D-allopyranoside prepared in Example 6. 151 mg of benzoyl chloride were added thereto and the mixture was stirred for 18 hours. After completion of the reaction, the reaction mixture was worked up give 333.5 mg of methyl-4,6-O-benzylidene-2-deoxy-2-fluoro-3-benzoyl-α-D-allopyranoside.

Rf=0.5 (toluene:ethyl acetate=6:1)
NMR (CDCl$_3$, ppm) 7.23–8.15 (m, 10H, 2xPh), 6.14 (d,d,d, 1H, H-3) 5.24 (s, 1H, Ph—CH), 4.97 (d, 1H, H-1) 4.73 (d, d, d, 1H, H-2, $J_{H-2-F}$=43.5 Hz, $J_{H-2-H-3}$=$J_{H-2-H-1}$=3.7 Hz) 4.26–4.41 (m, 2H, H-5, H-6a) 3.69–3.80 (m, 2H, H-4, H-6b), 3.57 (s, 3H, —OCH$_3$)

EXAMPLE 8

Preparation of
methyl-4,6-O-benzylidene-2-deoxy-2-fluoro-3-O-methansulfonyl-β-D-glucopyranoside (formula 12)

In 1 ml of pyridine were dissolved 200 mg of methyl-4,6-O-benzylidene-2-deoxy-2-fluoro-β-D-glucopyranoside. 0.2 ml of methansulfonyl chloride were added thereto and the mixture was reacted at room temperature overnight. After adding cold water thereto, the mixture was extracted with dichloromethane, washed with 5% solution of potassium bisulfate, water and then saturated saline, successively, and distilled under the reduced pressure. The residues were purified by silica gel column chromatography using toluene:ethyl acetate=6:1 as an eluant to give 217 mg of methyl-4,6-O-benzylidene-2-deoxy-2-fluoro-3-O-methansulfonyl-β-D-glucopyranoside.

Rf=0.4 (toluene:ethyl acetate=6:1)
NMR (CDCl$_3$, ppm) 7.42 (m, 5H, Ph), 5.53 (s, 1H, Ph—CH) 4.90 (d,d,d, 1H, H-3), 4.37 (d,d,d, 1H, H-2) 3.59 (s, 3H, —OCH$_3$), 3.01 (s, 3H, —CH$_3$)

EXAMPLE 9

Preparation of
methyl-4,6-O-benzylidene-2-deoxy-2-fluoro-3-O-benzoyl-β-D-allopyranoside (formula 13-1)

In 10 ml of dimethylformamide were dissolved 182 mg of methyl-4,6-O-benzylidene-2-deoxy-2-fluoro-3-O-methansulfonyl-β-D-glucopyranoside. 361 mg of sodium benzoate were added thereto and the mixture was heated for 12 hours and then cooled.

The reaction solution was concentrated under the reduced pressure to remove dimethylformamide, and the residues were extracted with dichloromethane and washed with water and then saturated saline.

After the concentration under the reduced pressure, the residue were purified by silica gel column chromatography to give 144 mg of methyl-4,6-O-benzylidene-2-deoxy-2-fluoro-3-O-benzoyl-β-D-allopyranoside.

Rf=0.3 (hexane:acetone=3:1)
NMR (CDCl$_3$, ppm) 7.24–8.08 (m, 10H, 2xPh), 6.17 (d,d,d, 1H, H-3) 5.54 (s, 1H, Ph-CH) 4.91 (d,d, 1H, H-1, $J_{H-1-H-2}$=7.8 Hz, $J_{H-1-F}$=2.4 Hz) 4.45 (d,d,d, 1H, H-2, $J_{H-2-H-3}$=3.4 Hz, $H_{H-2-F}$=45.6 Hz) 3.61 (s, 3H, —OCH$_3$)

EXAMPLE 10

Preparation of
methyl-2-deoxy-2-fluoro-3,4-di-O-benzoyl-6-deoxy-6-bromo-β-D-allopyranoside (formula 14-1)

In 8 ml of carbon tetrachloride were dissolved 200 mg of methyl-4,6-O-benzylidene-2-deoxy-2-fluoro-3-O-benzoyl-β-D-allopyranoside prepared in Example 9. 111.2 mg of N-bromosuccinimide and 150 mg of barium carbonate were added thereto and the mixture was refluxed for 2 hours. The reaction solution was filtered and the filtrate was washed with saturated aqueous sodium bicarbonate solution, water and then saturated saline, successively. After concentrating under the reduced pressure, the residues were purified by silica gel column chromatography (hexane : acetone=3:1) to give 200 mg of methyl-2-deoxy-2-fluoro-3,4-di-O-benzoyl-6-deoxy-6-bromo-β-D-allopyranoside.

Rf=0.3 (hexane:acetone=3:1)
NMR (CDCl$_3$, ppm) 7.24–8.01 (m, 10H, 2xPh), 6.19 (d,d,d, 1H, H-3) 5.20 (d,d,d, 1H, H-4) 5.02 (d,d, 1H, H-1, $J_{H-1-H-2}$=7.7 Hz, $J_{H-1-F}$=1.8 Hz) 4.60 (d,d,d, 1H, H-2, $J_{H-2-H-3}$=3.3 Hz, $J_{H-2-F}$=46.2 Hz) 3.67 (s, 3H, —OCH$_3$)

EXAMPLE 11

Preparation of
methyl-2-deoxy-2-fluoro-3,4-di-O-benzoyl-β-D-ribohex-5-enopyranoside (formula 15-1)

In 3.6 ml of pyridine were dissolved 180 mg of methyl-2-deoxy-2-fluoro-3,4-di-O-benzoyl-6-deoxy-6-bromo-βD-allopyranoside prepared in Example 10. 174 mg of silver fluoride were added thereto and the mixture was stirred at room temperature overnight. The reaction solution was filtered and the filtrate was washed with 10% solution of potassium bisulfate, water and then saturated saline, successively. After concentrating under the reduced pressure, the residues were purified by silica gel column chromatography using hexane:acetone=3:1 as an eluant to give 131 mg of methyl-2-deoxy-2-fluoro-3,4-di-O-benzoyl-β-D-ribohex-5-enopyranoside.

Rf : 0.4 (hexane:acetone=3:1)
NMR (CDCl$_3$, ppm) 7.24–8.09 (m, 10H, 2xPh) 6.00 (d,d, 1H, H-4) 5.64 (d,d, 1H, H-3, $J_{H-3-F}$=29 Hz) 5.16 (d,d, 1H, H-1) 4.97 (m, 2H, =CH$_2$) 4.85 (d,d,d,d, 1H, H-2) 3.53 (s, 3H, —OCH$_3$)

EXAMPLE 12

Preparation of
methyl-2,6-dideoxy-2-fluoro-3,4-di-O-benzoyl-α-L-talopyranoside(formula 16-1)

In 3.2 ml of methanol were dissolved 137 mg of methyl-2-deoxy-2-fluoro-3,4-di-O-benzoyl-β-D-ribohex-5-enopyranoside prepared in Example 11. 9.8 mg of 10% palladium/carbon were added thereto and the mixture was reacted at normal pressure under hydrogen stream for 5 hours. The reaction solution was filtered and the filtrate was concentrated under the reduced pressure. The resulting residues were purified by silica gel column chromatography using dichloromethane as an eluant to give 64 mg of methyl-2,6-dideoxy-2-fluoro-3,4-di-O-benzoyl-L-talopyranoside. There were also obtained 53 mg of methyl-2,6-dideoxy-2-fluoro-3,4-di-O-benzoyl-β-D-allopyranoside.

Rf=0.5 for L-talopyranoside derivative(methylene chloride) 0.3 for D-allopyranoside derivative(methylene chloride)

L-Talopyranoside derivative (H—NMR)

H—NMR (CDCl$_3$, ppm) 7.24–8.15 (m, 10H, 2xPh) 5.56 (d,d, 1H, H-4), 5.49 (d,d,d, 1H, H-3) 5.04 (d,d, 1H, H-1), 4.75 (ddt, 1H, H-2, $J_{H-2-F}$=48.7 Hz) 4.27 (qd, 1H, H-5), 3.47 (s, 3H, —OCH$_3$) 1.27 (d, 3H, —CH$_3$), C$^{13}$—NMR (CDCl$_3$, ppm) 166.4, 165.3 (2xCarbonyl) 133.2, 133.1, 130.1, 128.8, 128.4, 128.3 129.3, 128.8 (2xph), 99.1 (d, C-1, $J_{C-1-F}$=29.6 Hz) 85.1 (d, —2, $J_{C-2-F}$=182.8 Hz), 69.6 (C-4) 67.7 (d, C-3, $J_{C-3-F}$=15.4 Hz), 65.2 (C-5) 55.4 (—OCH$_3$), 16.3 (—CH$_3$)

D-Allopyranoside derivative ($^1$H—NMR) 7.21–8.02 (m, 5H, 2xPh) 6.14 (d,d,d, 1H, H-3) 4.94 (m, 2H, H-1, H-4) 4.54 (d,d,d, 1H, H-2, $J_{H-2-F}$=49.7 Hz, $J_{H-2-H-3}$=3.4 Hz) 4.21 (q, d, 1H, H-5), 3.62 (s, 3H, —OCH$_3$) 1.30 (d, 3H, —CH$_3$)

EXAMPLE 13

Preparation of methyl-2,6-dideoxy-2-fluoro-α-fluoro-α-L-talopyranoside(formula 17-1)

In 3 ml of methanol were dissolved 137 mg of methyl-2,6-dideoxy-2-fluoro-3,4-di-O-benzoyl-α-L-talopyranoside, 150 µl of 28% sodium methoxide were added thereto and the mixture was stirred at room temperature for 10 hours. The reaction solution was neutralized with IRC-50 resins and filtered, and the filtrate was concentrated under the reduced pressure. The residues were purified by silica gel column chromatography to give 58.5 mg of methyl-2,6-dideoxy-2-fluoro-α-L-talopyranoside.

Rf=0.4 (chloroform:methanol=15:1)

NMR (CDCl$_3$, ppm) 4.86 (d,d, 1H, H-1), 4.57 (d,d,d,d, 1H, H-2, $J_{H-2-F}$=49.2 Hz) 3.38 (s, 3H, —OCH$_3$), 1.25 (d, 3H, —CH$_3$)

EXAMPLE 14

Preparation of methyl-2-deoxy-2-fluoro-3,4-di-O-benzoyl-6-deoxy-6-bromo-α-D-allopyranoside (formula 14-2)

By following the procedure in Example 10 except that 100.8 mg of methyl-4,6-O-benzylidene-2-deoxy-2-fluoro-3-benzoyl-α-D-allopyranoside prepared in Example 7 were employed, there were obtained 110.8 mg(91%) of methyl-2-deoxy-2-fluoro-3,4-di-O-benzoyl-6-deoxy-6-bromo-α-D-allopyranoside.

Rf=0.4 (n-hexane:ethyl acetate=4:1)

NMR (CDCl$_3$, ppm) 7.20–8.01 (m, 10H, 2xPh), 6.16 (d,d,d, 1H, H-3) 5.19 (d,d,d,d, 1H, H-4), 5.08 (d, 1H, H-1) 4.79 (d,d,d, 1H, H-2, $J_{H-2-F}$=43.7 Hz, $J_{H-2-H-1}$=$J_{H-2-H-3}$=3.8 Hz) 4.52 (d,d,d, 1H, H-5), 3.66 (s, 3H, —OCH$_3$) 3.42–3.63 (m, 2H, H-6)

EXAMPLE 15

Preparation of methyl-2-deoxy-2-fluoro-3,4-di-O-benzoyl-α-D-ribohex-5-enopyranoside (formula 15-2)

By following the procedure in Example 11 except that 100 mg of methyl-2-deoxy-2-fluoro-3,4-di-O-benzoyl-6-deoxy-6-bromo-α-D-allopyranoside prepared in Example 14 were employed, there were obtained methyl-2-deoxy-2-fluoro-3,4-di-O-benzoyl-α-D-ribohex-5-enopyranoside in a quantatitive yield.

Rf=0.3 (n-hexane:ethyl acetate=4:1)

NMR (CDCl$_3$, ppm) 7.24–8.04 (m, 10H, 2XPh) 5.80–5.89 (m, 2H, H-3, H-4) 4.83–5.07 (m, 4H. H-1, H-2, =CH$_2$) 3.66 (S, 3H, —OCH$_3$)

EXAMPLE 16

Preparation of methyl-2,6-dideoxy-2-fluoro-3,4-di-O-benzoyl-β-L-talopyranoside(formula 16-2)

By following the procedure in Example 12 except that 80 mg of methyl-2-deoxy-2-fluoro-3,4-di-O-benzoyl-α-D-ribohex-5-enopyranoside prepared in Example 15 were employed, there were obtained methyl-2,6-dideoxy-2-fluoro-3,4-di-O-benzoyl-β-L-talopyranoside in a quantatitive yield.

Rf=0.2 (n-hexane:ethyl acetate=4:1)

NMR (CDCl$_3$, ppm) 7.27–8.16 (m, 10H, 2xPh), 5.54 (d, 1H, H-4) 5.26 (d,d,d, 1H, H-3, $J_{H-3-F}$=30.1 Hz) 4.87 (d, m, 1H, H-2, $J_{H-2-F}$=51.8 Hz) 4.55 (d, 1H, H-1, $J_{H-1-F}$=18.8 Hz) 3.95 (d, q, 1H, H-5), 3.66 (s, 3H, —OCH$_3$) 1.35 (d, 3H, —CH$_3$)

EXAMPLE 17

Preparation of methyl-2,6-dideoxy-2-fluoro-β-L-talopyranoside(formula 17-2)

By following the procedure in Example 13 except that 110 mg of methyl-2,6-dideoxy-2-fluoro-3,4-di-O-benzoyl-β-L-talopyranoside prepared in Example 16 were employed, there were obtained 47 mg of methyl-2,6-dideoxy-2-fluoro-β-L-talopyranoside.

Rf=0.3 (chloroform:methanol:15:1)

NMR (CDCl$_3$, ppm) 4.70 (d,m, 1H, H-2, $J_{H-2-F}$=51 Hz) 4.30 (d, 1H, H-1, $J_{H-1-F}$=20 Hz), 3.58 (s, 3H, —OCH$_3$) 3.46–3.66 (m, 3H, H-3, H-4, H-5), 3.07 (d, 1H, —OH) 1.87 (d,d, 1H, —OH), 1.38 (d, 3H, —CH$_3$)

EXAMPLE 18

Preparation of 1,3,4-tri-O-acetyl-2,6-dideoxy-2-fluoro-α-L-talopyranose

In 1.5 ml of nitromethane were dissolved 50 mg of methyl-2,6-dideoxy- 2-fluoro-β-L-talopyranoside prepared in Example 17. 0.26 ml of anhydrous acetic acid and 7.3 µl of sulfuric acid were added thereto and the mixture was stirred at normal temperature for 6 hours. The reaction solution was neutralized with saturated sodium bicarbonate solution and extracted with chloroform. The chloroform layer was washed with water and saturated saline, successively and concentrated under the reduced pressure. The residues were purified by silica gel column chromatography using toluene:ethyl acetate=6:1 as an eluant to give 67 mg of the desired compound.

Rf=0.2 (toluene:ethyl acetate=6:1)

REFERENCE EXAMPLE 1

Preparation of 1,3,4-tri-O-acetyl-2,6-dideoxy-2-fluoro-α-L-talopyranose

In 1.5 ml of nitromethane were dissolved 50 mg of methyl-2,6-dideoxy-2-fluoro-α-L-talopyranoside prepared in Example 13. 0.26 ml of anhydrous acetic acid and 7.3 µl of sulfuric acid were added thereto and the mixture was stirred at normal temperature for 6 hours. The reaction solution was neutralized with saturated sodium bicarbonate solution and extracted with chloroform. The chloroform layer was washed with water and saturated saline, successively and concentrated under the reduced pressure. The residues were purified by silica gel column chromatography using toluene:ethyl acetate=6:1 as an eluant to give 50 mg of the desired compound.

Rf=0.2 (toluene:ethyl acetate=6:1)

REFERENCE EXAMPLE 2

Preparation of 3,4-di-O-acetyl-2,6-dideoxy-2-fluoro-α-L-talopyranosyl-bromide

In a mixed solvent (14 ml) of anhydrous methylene chloride and anhydrous ethyl acetate (10:1) were dissolved 654 mg of 1,3,4-tri-O-acetyl-2,6-dideoxy-2-fluoro-α-L-talopyranose.

1.07 g of titanium tetrabromide were added thereto and the mixture was allowed to react at room temperature for 22 hours.

To the reaction solution, 20 ml of anhydrous acetonitrile, 3.34 g of sodium acetate and 40 ml of anhydrous toluene were added successively.

The resulting precipitates were filtered off and the filtrate was concentrated under the reduced pressure. Further 40 ml of toluene were added to the residues to remove insolubles and the filtrate was concentrated under the reduced pressure to give 660 mg of the desired compound.

Specific rotation $[\alpha]_D^{25}$: −154° (c:1, chloroform)

REFERENCE EXAMPLE 3

Preparation of 7-O-(3,4-di-O-acetyl-2,6-dideoxy-2-fluoro-α-L-talopyranosyl) daunomycinon In 36 ml of anhydrous methylene chloride were suspended 290 mg of daunomycinon, 943 mg of mercuric oxide (yellow), 273 mg of mercuric bromide and 4.5 g of powdery molecular sieve 3A, and a solution of 330 mg of 3,4-di-O-acetyl-2,6-dideoxy-2-fluoro-α-L-talopyranosyl bromide in 9 ml of anhydrous methylene chloride was added thereto. The reaction mixture was stirred at room temperature in the dark for 20 hours and filtered. The filtrate was diluted with chloroform, washed with 30% aqueous potassium iodide solution, saturated sodium bicarbonate solution and the water, successively and concentrated. The residues were purified by silica gel column chromatography using benzene:acetone=4:1 as an eluant to give 370 mg of the desired compound in red solids.

m.p.: 144°–146° C.

Specific rotation $[\alpha]_D^{26}$: +211° (c:0.036, chloroform)

REFERENCE EXAMPLE 4

Preparation of 7-O-(2,6-dideoxy-2-fluoro-α-L-talopyranosyl) daunomycinon

In 8 ml of 0.2N-aqueous caustic soda solution were dissolved 100 mg of 7-O(3,4-di-O-acetyl-2,6-dideoxy-2-fluoro-α-L-talopyranosyl) daunomycinon prepared in Reference Example 3 and the solution was allowed to react at 0° C. for 30 min. The reaction solution was neutralized with 1N-aqueous hydrochloric acid solution at 0° C. and extracted with methylene chloride. The extract was washed with saturated saline and concentrated. The resulting red solids were reprecipitated with chloroform and hexane to give 63 mg(72%) of the desired compound.

Specific rotation $[\alpha]_D^{25}$: +197° (c:0.02, chloroform:methanol=1:1)

REFERENCE EXAMPLE 5

Preparation of 7-O-(2,6-dideoxy-2-fluoro-α-L-talopyranosyl) adriamycinon

In a mixed solvent of 4.6 ml of absolute methanol and 7 ml of anhydrous dioxane were suspended 190 mg of 7-O-(2,6-dideoxy-2-fluoro-α-L-talopyranosyl) daunomycinon prepared in Reference Example 4. 0.26 ml of methyl orthoformate were added thereto and the mixture was allowed to react. The reaction suspension was cooled to 0° C., a solution of 75 mg of bromine water in 0.75 ml of anhydrous methylene chloride was added thereto, and the mixture was allowed to react for 1 hour and stirred at room temperature for 2 hours. The red precipitates formed by addition of 60 ml of isopropyl ether were recovered by centrifugation and washed twice with isopropyl ether. The precipitates were suspended in 15 ml of acetone and stirred at room temperature for 40 min. 25 ml of isopropyl ether and 10 ml of hexane were added to the homogeneous solution to give precipitates, which were centrifuged to give red solids.

The solids were dissolved in a mixed solvent of 16 ml of acetone and 4 ml of water, 325 mg of sodium formate were added thereto and the mixture was stirred at room temperature for 20 hours. The reaction solution was concentrated and the resulting solid residues were washed with water and dried. The residues were dissolved in 15 ml of 40% aqueous acetic acid solution and allowed to react at 80° C. for 4 hours followed by concentration under the reduced pressure. The residues, to which water was added, were centrifuged and re-precipitated with chloroform:methanol:isopropyl ether to give 84 mg(43%) of the desired compound.

Specific rotation $[\alpha]_D^{25}$: +194° (c:0.01, chloroform:methanol=1:1)

REFERENCE EXAMPLE 6

Preparation of 7-O-(2,6-dideoxy-2-fluoro-3,4-O-isopropylidene-α-L-talopyranosyl) adriamycinon-14-O-pimelate In a mixed solvent of 10 ml of acetone and 2.5 ml of water were dissolved 100 mg of 14-bromo-7-O-(2,6-dideoxy-2-fluoro-3,4-O-isopropylidene-α-L-talopyranosyl) daunomycinon, 490 mg of monosodium pimelate were added thereto and the mixture was vigorously stirred for 17 hours. The reaction solution was concentrated under the reduced pressure to evaporate acetone and extracted with chloroform. The chloroform layer was washed with water and concentrated under the reduced pressure. The residues were purified by silica gel column chromatography using benzene:acetone=5:1 as an eluant to give 72 mg of the desired compound.

Specific rotation $[\alpha]_D^{25}$: +64° (c:0.13 CHCl$_3$)
m.p.: 131°–137° C.

REFERENCE EXAMPLE 7

Preparation of 7-O-(2,6-dideoxy-2-fluoro-α-L-talopyranosyl) adriamycinon-14-O-pimelate In 6 ml of 80% aqueous acetic acid solution were dissolved 76 mg 7-O-(2,6-dideoxy-2-fluoro-3,4-O-isopropylidene-α-L-talopyranosyl) adriamycinon prepared in Reference Example 6 and the solution was stirred at 70° C. for 40 min. The reaction solution was concentrated under the reduced pressure and the residues were purified by silica gel column chromatography using chloroform:methanol=10:1 as an eluant to give 58 mg of the desired compound.

m.p. : 108°–113° C.

Specific rotation $[\alpha]_D^{25}$: +161° (c:0.056 chloroform: methanol=1:1)

REFERENCE EXAMPLE 8

Preparation of 7-O-(2,6-dideoxy-2-fluoro-3,4-O-isopropylidene-α-L-talopyranosyl) adriamycinon-14-O-t-butyloxycarbonylglycinate In a mixed solvent of 26 ml of acetone and 8 ml of water were dissolved 180 mg of 14-bromo-7-O-(2,6-dideoxy-2-fluoro-3,4-O-isopropylidene-α-L-talopyranosyl) daunomycinon, 1.5 g of sodium-t-butyloxycarbonyl glycinate were added thereto and the mixture was stirred at room temperature for 20 hours. The reaction solution was distilled under the reduced pressure to remove acetone. The residues were extracted with chloroform, washed with water and then saturated saline, successively and concentrated to dryness under the reduced pressure. The resulting residues were purified by silica gel column chromatography using chloroform:methanol=20:1 as an eluant to give 121 mg of the desired compound.

m.p. : 142°–143.5° C.

Specific rotation $[\alpha]_D^{20}$: +77° (c:0.026, chloroform)

REFERENCE EXAMPLE 9

Preparation of 7-O-(2,6-dideoxy-2-fluoro-α-L-talopyranosyl) adriamycinon-14-O-glycinate hydrochloride In 1.5 ml of chloroform were dissolved 120 mg of 7-O-(2,6-dideoxy-2-fluoro-3,4-O-isopropylidene-α-L-talopyranosyl) adriamycin-14-O-t-butylcarbonylglycinate prepared in Reference Example 8 at room temperature and then 15 ml of methanol were dissolved therein. 12 ml of saturated hydrochloric ether solution were added thereto and the mixture was stirred for 4 hours.

After completion of the reaction, the reaction solution was concentrated and ether was added to give solids, which were filtered and dried to give 84 mg of the desired compound.

m.p. : 179°–185° C.

What is claimed is:

1. A process for preparing a compound of formula (17-1):

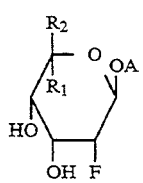
(17-1)

wherein, A is hydrogen, a lower alkyl group having 1 to 5 carbon atoms, or a hydroxyl-protecting group; and $R_1$ and $R_2$ are, independently, hydrogen or a lower alkyl group having 1 to 5 carbon atoms, which process comprises subjecting a compound of formula (12):

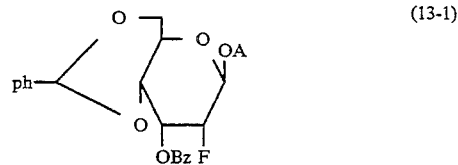
(12)

wherein, $B_2$ is a hydroxyl-leaving group; Ph is phenyl; and A has the same meanings as defined above, to substitution in the presence of sodium benzoate in dimethyl formamide to give a compound of formula (13-1):

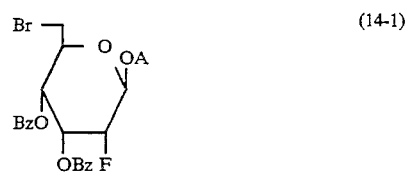
(13-1)

wherein, Bz is benzoyl; and A and Ph have the same meanings as defined above, subjecting the compound of formula (13-1) to bromobenzoylation in the presence of N-bromosuccinimide and barium carbonate in carbon tetrachloride to give a compound of formula (14-1):

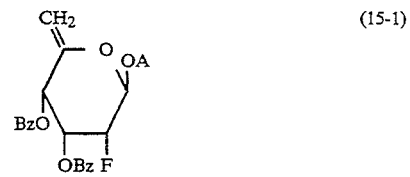
(14-1)

wherein A and Bz have the same meanings as defined above, reacting the compound of formula (14-1) with a metal halide in an amine to give a compound of formula (15-1):

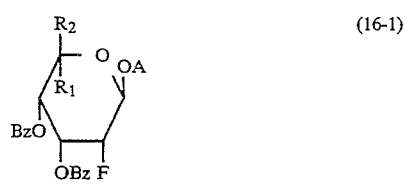
(15-1)

wherein A and Bz have the same meanings as defined above, subjecting the compound of formula (15-1) to hydrogenation in the presence of a metal catalyst selected from the group consisting of palladium, Raney-nickel and platinum, to give a compound of formula (16-1):

(16-1)

wherein, A, $R_1$, $R_2$, and Bz have the same meanings as defined above, and subjecting the compound of formula (16-1) to debenzoylation in the presence of sodium methoxide in methanol to give the compound of the formula (17-1).

* * * * *